(12) United States Patent
Yoda et al.

(10) Patent No.: US 10,475,213 B2
(45) Date of Patent: Nov. 12, 2019

(54) X-RAY CT APPARATUS AND IMAGE PROCESSING APPARATUS

(71) Applicant: Toshiba Medical Systems Corporation, Otawara-shi (JP)

(72) Inventors: Takahiro Yoda, Nasushiobara (JP); Katsuhito Morino, Utsunomiya (JP); Yojiro Suzuki, Otawara (JP); Katsuhiko Ishida, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/810,838

(22) Filed: Jul. 28, 2015

(65) Prior Publication Data
US 2016/0027192 A1    Jan. 28, 2016

(30) Foreign Application Priority Data

Jul. 28, 2014 (JP) .................................. 2014-153334
Jul. 27, 2015 (JP) .................................. 2015-147771

(51) Int. Cl.
G06T 11/00 (2006.01)
G01N 23/046 (2018.01)
G06T 3/40 (2006.01)

(52) U.S. Cl.
CPC .......... *G06T 11/003* (2013.01); *G01N 23/046* (2013.01); *G06T 3/40* (2013.01)

(58) Field of Classification Search
CPC ........ G01N 23/046; G06T 11/003; G06T 3/40
See application file for complete search history.

(56) References Cited

U.S. PATENT DOCUMENTS

2007/0081708 A1* 4/2007 Hempel .................. G06T 19/00
 382/128
2008/0279439 A1* 11/2008 Minyard .............. A61B 5/0002
 382/131

(Continued)

FOREIGN PATENT DOCUMENTS

JP         04295340 A   * 10/1992
JP         2002-143150      5/2002
JP         2003-19131       1/2003

(Continued)

*Primary Examiner* — Gandhi Thirugnanam
(74) *Attorney, Agent, or Firm* — Oblon, McClelland, Maier & Neustadt, L.L.P.

(57) ABSTRACT

An X-ray computed tomography (CT) apparatus according to an embodiment includes processing circuitry. The processing circuitry causes a CT image designated as a display object image to be displayed on a display, every time any of a plurality of reconstructed CT images is designated as the display object image. The processing circuitry causes a newly reconstructed enlarged CT image to be displayed on the display when the processing circuitry receives an enlargement instruction to enlarge the CT image displayed on the display. The processing circuitry performs preprocessing on raw data corresponding to the CT image designated as the display object image, every time any of the CT images is designated as the display object image. The processing circuitry reconstructs the enlarged CT image using the preprocessed raw data, based on the enlargement instruction, when the processing circuitry receives the enlargement instruction.

14 Claims, 13 Drawing Sheets

(56) References Cited

U.S. PATENT DOCUMENTS

| | | | | |
|---|---|---|---|---|
| 2009/0097778 A1* | 4/2009 | Washburn | ............... | A61B 90/36 |
| | | | | 382/294 |
| 2010/0156898 A1* | 6/2010 | Voros | ................. | A61B 5/02007 |
| | | | | 345/419 |
| 2011/0280366 A1* | 11/2011 | Maeda | .................... | A61B 6/032 |
| | | | | 378/8 |
| 2012/0148125 A1* | 6/2012 | Dekel | .................... | G06T 11/006 |
| | | | | 382/128 |
| 2012/0201436 A1* | 8/2012 | Oakley | ................. | G06T 3/4053 |
| | | | | 382/128 |
| 2014/0328524 A1* | 11/2014 | Hu | ........................ | G06F 19/321 |
| | | | | 382/128 |
| 2015/0030221 A1* | 1/2015 | Lou | ........................ | G06T 3/0068 |
| | | | | 382/131 |
| 2015/0278993 A1* | 10/2015 | Yamazaki | .................. | G06T 3/40 |
| | | | | 345/660 |
| 2015/0317766 A1* | 11/2015 | Naganawa | ................. | G06T 3/40 |
| | | | | 345/668 |
| 2015/0347682 A1* | 12/2015 | Chen | ....................... | G16H 50/30 |
| | | | | 705/2 |
| 2016/0027192 A1* | 1/2016 | Yoda | ..................... | G06T 11/003 |
| | | | | 382/131 |
| 2016/0081646 A1* | 3/2016 | Yoda | ...................... | A61B 6/463 |
| | | | | 378/4 |

FOREIGN PATENT DOCUMENTS

| | | |
|---|---|---|
| JP | 2004-180990 | 7/2004 |
| JP | 2005-245914 | 9/2005 |
| JP | 2014-117311 | 6/2014 |
| JP | 2014-239814 | 12/2014 |

* cited by examiner

X-RAY CT APPARATUS AND IMAGE PROCESSING APPARATUS

CROSS-REFERENCE TO RELATED APPLICATIONS

This application is based upon and claims the benefit of priority from Japanese Patent Application No. 2014-153334, filed on Jul. 28, 2014, the entire contents of all of which are incorporated herein by reference. The entire contents of the prior Japanese Patent Application No. 2015-147771, filed on Jul. 27, 2015, are also incorporated herein by reference.

FIELD

Embodiments described herein relate generally to an X-ray CT apparatus and an image processing apparatus.

BACKGROUND

Conventionally, there exist X-ray CT apparatuses in which an already reconstructed computed tomography (CT) image is displayed on a display unit. When such an X-ray CT apparatus receives an enlargement instruction to enlarge the displayed CT image, the X-ray CT apparatus reconstructs an enlarged CT image in accordance with the enlargement instruction, to cause the display unit to display the reconstructed enlarged CT image.

For example, when an X-ray CT apparatus receives an enlargement instruction, the X-ray CT apparatus reads raw data that was used in reconstruction of the displayed CT image from a storage, and subjects the read raw data to preprocessing. Then, the X-ray CT apparatus reconstructs the enlarged CT image complying with the enlargement conditions included in the enlargement instruction, using the preprocessed raw data.

However, the above X-ray CT apparatuses may require much time, because various types of processing such as preprocessing are performed from input of an enlargement instruction to reconstruction of an enlarged CT image. For this reason, the above X-ray CT apparatuses may fail to promptly reconstruct an enlarged CT image.

DETAILED DESCRIPTION

An X-ray computed tomography (CT) apparatus according to an embodiment includes processing circuitry. The processing circuitry causes a CT image designated as a display object image to be displayed on e display, every time any of a plurality of reconstructed CT images is designated as the display object image. The processing circuitry causes a newly reconstructed enlarged CT image to be displayed on the display when the processing circuitry receives an enlargement instruction to enlarge the CT image displayed on the display. The processing circuitry performs preprocessing on raw data corresponding to the CT image designated as the display object image, every time any of the CT images is designated as the display object image. The processing circuitry reconstructs the enlarged CT image using the preprocessed raw data, based on the enlargement instruction, when the processing circuitry receives the enlargement instruction.

The following is detailed explanation of embodiments of the X-ray CT apparatus with reference to the attached drawings.

First Embodiment

Figure 1:
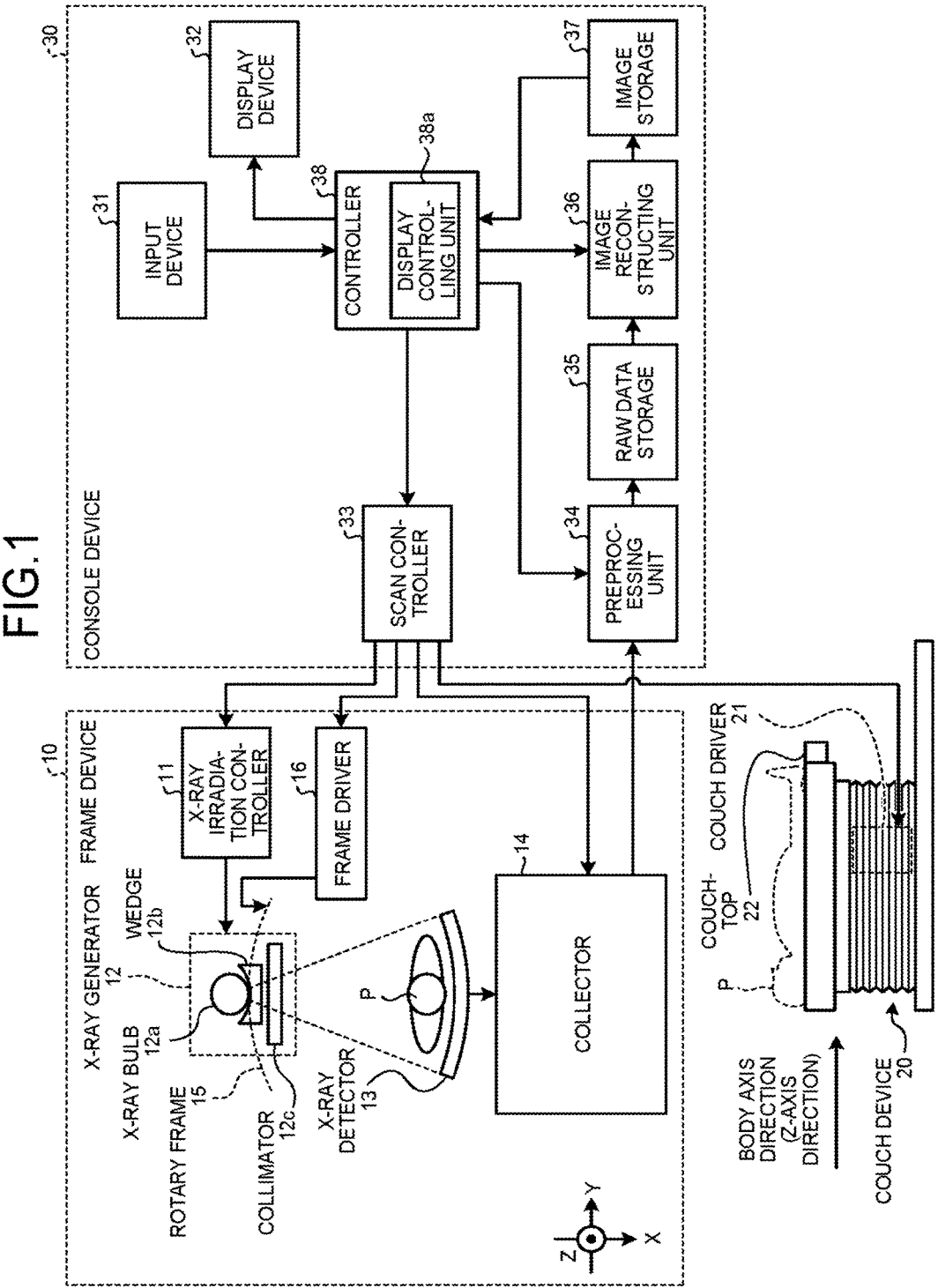
FIG. 1 is a diagram illustrating a configuration example of an X-ray CT apparatus according to a first embodiment.

First, the configuration of the X-ray CT apparatus according to a first embodiment will be explained hereinafter. FIG. 1 is a diagram illustrating a configuration example of the X-ray CT apparatus according to the first embodiment. As illustrated in FIG. 1, the X-ray CT apparatus according to the first embodiment includes a frame device 10, a couch device 20, and a console device 30.

The frame device 10 applies X-rays to a subject P, and collects projection data from detection data of the X-rays having passed the subject P. The frame device 10 includes an X-ray irradiation controller 11, an X-ray generator 12, an X-ray detector 13, a collector 14, a rotary frame 15, and a frame driver 16.

The rotary frame 15 supports the X-ray generator including an X-ray bulb 12a described later and the X-ray detector 13 to be rotatable around the subject P. The rotary frame 15 is a circular frame that supports the X-ray generator 12 and the X-ray detector 13 to face each other with the subject P interposed therebetween, and rotates at high speed along a circular track with the subject P serving as the center by the frame driver 16 described later.

The X-ray generator 1 is a device that generates X-rays and applies the generated X-rays to the subject P. The X-ray generator 12 includes the X-ray bulb 12a, a wedge 12b, and a collimator 12c.

The X-ray bulb 12a emits X-rays. Specifically, the X-ray bulb 12a is a vacuum tube that generates an X-ray beam to the subject P with a high voltage supplied from the X-ray irradiation controller 11 described later. The X-ray bulb 12a emits an X-ray beam to the subject P in accordance with rotation of the rotary frame 15. The X-ray bulb 12a generate an X-ray beam that spreads with a fan angle and a cone angle.

The wedge 12b is an X-ray filter to adjust the X-ray dose of the X-rays emitted from the X-ray bulb 12a. The collimator 1 is a slit to narrow the irradiation range of the X-rays having an X-ray dose adjusted by the wedge 12b, under the control of the X-ray irradiation controller 11 described later.

The X-ray irradiation controller 11 is a device that supplies the X-ray bulb 12a with high voltage as a high voltage generator. The X-ray bulb 12a generates X-rays using high voltage supplied from the X-ray irradiation controller 11. The X-ray irradiation controller 11 adjusts the X-ray dose applied to the subject P, by adjusting a tube voltage and a tube current supplied to the X-ray bulb 12a. The X-ray irradiation controller 11 also adjusts the irradiation range (far angle and cone angle) the X-rays by adjusting the aperture of the collimator 12c.

Control by the X-ray irradiation controller 11 enables the X-ray bulb 12a to continuously emit X-rays around the whole periphery of the subject P for full reconstruction, and continuously emit X-rays with an exposure range (180°+fan angle) that enables half reconstruction for half reconstruction. Control by the X-ray irradiation controller 11 also enables the X-ray bulb 12a to intermittently emit X-rays (pulse X-rays) at a preset position (the position of the bulb). The X-ray irradiation controller 11 is also capable of modulating the intensity of X-rays emitted from the X-ray bulb 12a. For example, the X-ray irradiation controller 11 increases the intensity of X-rays emitted from the X-ray bulb 12a at a specific bulb position, and decreases the intensity of the X-rays emitted from the X-ray bulb 12a in a range other than the specific bulb position. The bulb position means a position of the X-ray bulb 12a on the circular track with the subject P serving as the center. In the following explanation, the position (bulb position, bulb angle) of the X-ray bulb 12a illustrated in FIG. 1 is defined as "0° (360°)". In the following explanation, the bulb position (bulb angle) is defined as "0°, . . . , 90°, . . . , 180°, . . . , 270°, . . . , 360°"' clockwise along the circumferential direction of the rotary frame 15 illustrated in FIG. 1.

The frame driver 16 drives and rotates the rotary frame 15, to revolve the X-ray generator 12 and the X-ray detector 13 on the circular track with the subject P serving as the center.

The X-ray detector 13 detects X-rays emitted from the X-ray bulb 12a and having passed through the subject P. Specifically, the X-ray detector 13 detects X-rays emitted from the X-ray bulb 12a and having passed through the subject P, with X-ray detecting elements arranged in a two-dimensional manner. The X-ray detector 13 illustrated in FIG. 1 is a two-dimensional array detector (surface detector) that outputs X-ray intensity distribution data indicating an intensity distribution of the X-rays having passed through the subject P. The X-ray detector 13 includes a plurality of X-ray detecting elements (detecting element line) arranged in a channel direction (Y-axis direction illustrated in FIG. 1) and arranged in a plurality of lines along the body axis direction (Z-axis direction illustrated in FIG. 1) of the subject P. For example, the X-ray detector 13 includes detecting elements arranged in 320 lines along the body axis direction of the subject P, to detect a wide range of X-ray intensity distribution data having passed through the subject P.

The collector 14 is a data acquisition system (DAS) that collects projection data from X-ray detection data (X-ray intensity distribution data) detected by the X-ray detector 13. For example, the collector 14 performs amplification, A/D conversion, and sensitivity correction between channels and the like on the X-ray intensity distribution data detected by the X-ray detector 13, to generate projection data and transmit the generated projection data to the console device 30 described later. For example, when X-rays are continuously applied from the X-ray bulb 12a during rotation of the rotary frame, the collector 14 collects a projection data grub for the whole circumference (360°). The collector 14 also correlates each of the collected pieces of projection data with the bulb position, and transmits the data to the console device 30 described later. The bulb position serves as information indicating the projection direction of the projection data. A preprocessing unit 34 described later may perform the sensitivity correction between channels.

The couch device 20 is a device on which the subject P is placed. The couch device 20 includes a couchtop 22 and a couch driver 21. The couchtop is a plate on which the subject P is placed. The couch driver 21 moves the couchtop 22 in the Z-axis direction under the control of a scan controller 33 described later, to move the subject P into the rotary frame 15 (into the imaging space).

For example, the frame device 10 executes helical scan to helically scan the subject P by rotating the rotary frame 15 while the couchtop 22 is moved. As another example, the frame device 10 executes conventional scanning to scan the subject P with a circular track by rotating the rotary frame 15 with the position of the subject P fixed after the couchtop 22 is moved. As another example, the frame device 10 executes a step and shoot method in which the position of the couchtop 22 is moved at regular intervals to execute conventional scan in a plurality of scanning areas.

The console device 30 is a device that receives operations of the X-ray CT apparatus by the operator, and reconstructs CT image data from the projection data collected by the frame device 10. The console device 30 includes an input device 31, a display device 32, the scan controller 33, the preprocessing unit 34, a raw data storage 35, an image reconstructing unit 36, an image storage 37, and a controller 38.

The input device 31 includes a mouse, a keyboard, a button, or a pedal (foot switch) and the like used by the operator of the X-ray CT apparatus for inputting various instructions and settings. The input device 31 transmits information of instructions and settings received from the operator to the controller 38.

The display device 32 is a monitor that the operator refers to. The display device 32 displays CT image data under the control of the controller 38, and displays graphical user interface (GUI) to receive various instructions and settings from the operator via the input device 31. For example, the operator inputs inspection information, such as the body position of the subject P placed on the couchtop 22 in imaging, to the GUI for inspection information registration using the input device 31.

The scan controller 33 controls operations of the X-ray irradiation controller 11, the frame driver 16, the collector 14, and the couch driver 21 under the control of the controller 38 described later, to control projection data collection processing in the frame device 10.

The preprocessing unit 34 subjects the projection data collected by the collector 14 to correction processing such as logarithmic transformation, offset correction, sensitivity correction, and beam hardening correction, to generate corrected projection data. In the following explanation, the corrected projection data generated by the preprocessing unit 34 is referred to as "raw data". The beam hardening correction can be performed by a preprocessing unit 36c, not the preprocessing unit 34, for example.

The raw data storage 35 stores raw data generated by the preprocessing unit 34. The raw data storage 35 stores the bulb position in association with the raw data generated by the preprocessing unit 34.

Figure 2:
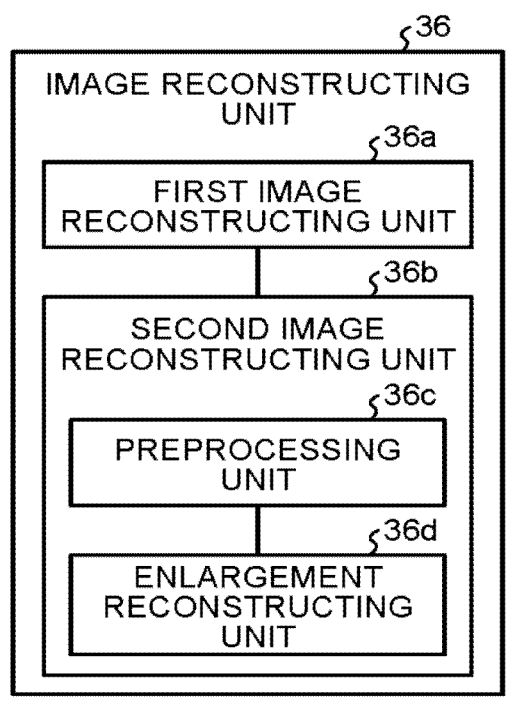
FIG. 2 is a diagram illustrating an example of the configuration of an image reconstructing unit according to the first embodiment.

The image reconstructing unit 36 is a processor that generates CT images using the raw data stored in the raw data storage 35. FIG. 2 is a diagram illustrating an example of the configuration of the image reconstructing unit according to the first embodiment. As illustrated in FIG. 2, the image reconstructing unit 36 includes a first image reconstructing unit 36a and a second image reconstructing unit 36b.

Figure 3:
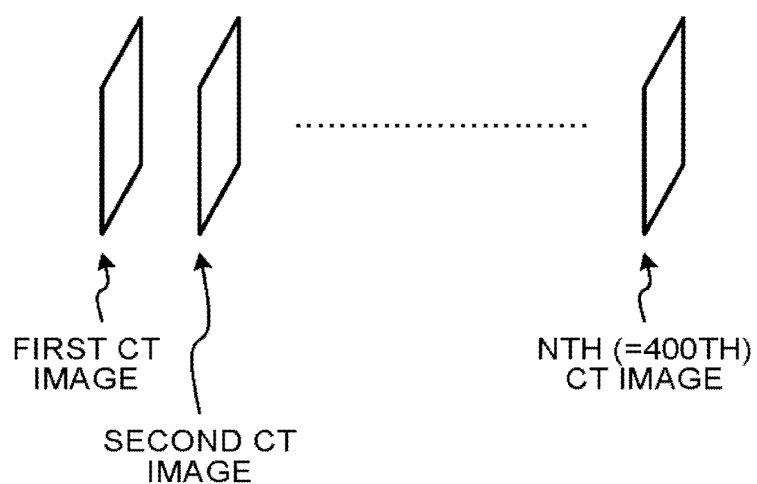
FIG. 3 is a diagram illustrating an example of CT images.

The first image reconstructing unit 36a reconstructs CT images using the raw data stored in the raw data storage 35. For example, when an image reconstructing instruction received from the operator is transmitted from the input device 31, the first image reconstructing unit 36a reconstructs N (N=400) CT images illustrated in FIG. 3. Various methods may be used as the reconstruction method, such as back projection. An example of back projection is back projection by filtered back projection (FBP).

Figure 4:
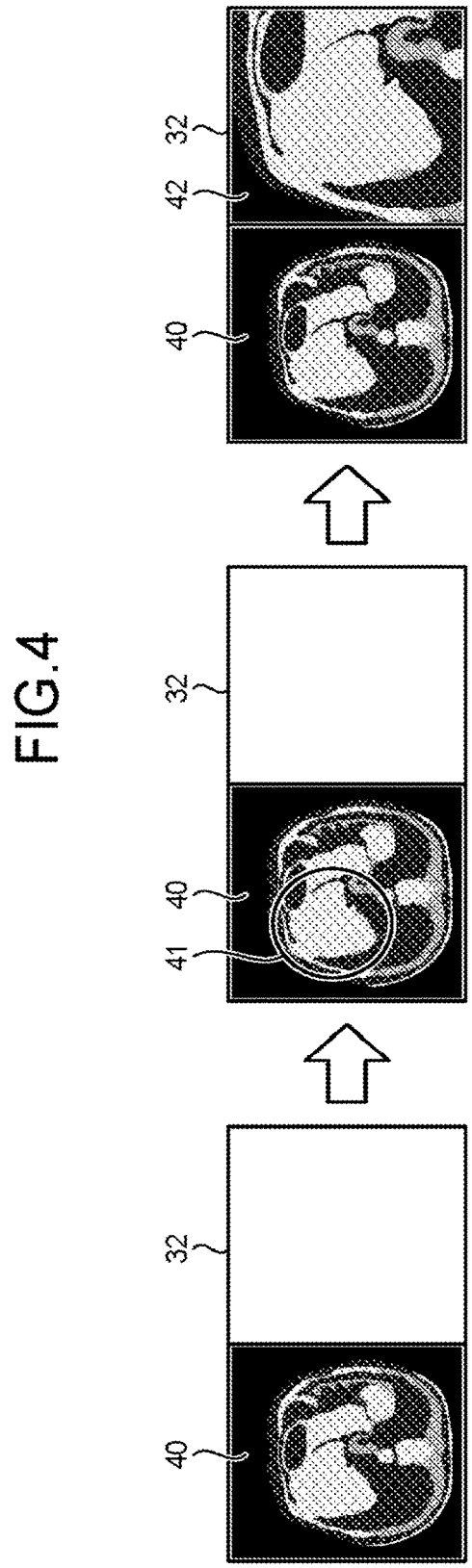
FIG. 4 is a diagram illustrating an example of transition of images displayed on a display device.

FIG. 4 is a diagram illustrating an example of transition of images displayed on the display device. As illustrated in the left part in FIG. 4, a CT image 40 reconstructed by the first image reconstructing unit 36a is displayed in a certain display region of the display device 32 under the control of a display controlling unit 38a described later.

The second image reconstructing unit 36b starts up a real time process to execute preprocessing and enlarged image reconstruction, when the operator designates any of a plurality of CT images reconstructed by the first image reconstructing unit 36a as an object image to be displayed on the display device 32. In the following explanation, an object image designated by the operator to be displayed on the display device 32 referred to as display object image. When the second image reconstructing unit 36b that starts up the real time process to execute preprocessing and enlarged image reconstruction is functionally illustrated, the second image reconstructing unit 36b includes the preprocessing unit 36c and an enlargement reconstructing unit 36d, as illustrated in FIG. 2.

The preprocessing unit 36c performs preprocessing on the raw data corresponding to the CT image designated as the display object image, every time any of the CT images reconstructed by the first image reconstructing unit 36a is designated as the display object image.

For example, every time any of the CT images is designated as the display object image, the preprocessing unit 36c reads the raw data used for reconstructing the CT image designated as the display object image from the raw data storage 35. For example, when the raw data is obtained by helical scan and the CT image designated as the display object image is an $M^{th}$ image, the preprocessing unit 36c performs the following processing. Specifically, the preprocessing unit 36c specifies a couchtop position (couch position) that is a position on the couchtop 22 where the raw data used for reconstructing the $M^{th}$ image determined from the moving speed of the couchtop 22 in helical scan and the like was scanned. The preprocessing unit 36c estimates the position in the whole raw data stored in the raw data rage 35, based on the specified couchtop position. Thereafter, the preprocessing unit 36c reads raw data located in the estimated position from the whole raw data stored in the raw data storage 35.

When the raw data is obtained by conventional scan (such as dynamic volume scan) and the CT image designated as the display object image is an $M^{th}$ image, the preprocessing unit 36c performs the following processing. Specifically, the preprocessing unit 36c specifies the time when the M image was scanned. The preprocessing unit 36c estimates the position in the whole raw data stored in the raw data storage 35, based on the specified time. Thereafter, the preprocessing unit 36c reads raw data located in the estimated position from the whole raw data stored in the raw data storage 35. The dynamic volume scan means continuous scan at a fixed couch position using multi-row detectors, for example.

When the raw data is read out, the preprocessing unit 3c subjects the read raw data to preprocessing such as noise reduction and scattered ray reduction. For example, the preprocessing unit 36c subjects the raw data to noise reduction, and performs scattered ray reduction on the raw data having been subjected to noise reduction. The preprocessing unit 36c may perform at least one of noise reduction and scattered ray reduction on the raw data as preprocessing.

Thereafter, the preprocessing unit 36c subjects the preprocessed raw data to convolution to reduce blurredness of the image. The preprocessing unit 36c may omit the convolution, performing only preprocessing on the raw data.

The preprocessing and convolution can be performed on the raw data without using enlargement conditions included in the enlargement instruction. For this reason, as described above, the preprocessing unit 36c performs preprocessing or convolution on the raw data, before the input device 31 receives an enlargement instruction from the operator.

Next, the preprocessing unit 36c stores the raw data having been subjected to preprocessing or convolution in a random access memory (RAM) included in the preprocessing unit 36c. When the RAM stores other raw data having been subjected to preprocessing or convolution, the preprocessing unit 36c erases the other raw data from the RAM, and thereafter stores new raw data having been subjected to preprocessing or convolution in the RAM. Specifically, in the present embodiment, the raw data corresponding to the CT image on display and serving as the object of the enlargement instruction is stored in the RAM after having been subjected to preprocessing or convolution. In addition, in the present embodiment, because the RAM stores only raw data corresponding to the CT image being displayed on the display device 32 and having been subjected to preprocessing or convolution, the present embodiment suppresses occurrence of a phenomenon such as a problem in that the capacity of the RAM is encumbered.

When the enlargement reconstructing unit 36d receives an enlargement instruction, the enlargement reconstructing unit 36d reconstructs an enlarged CT image using raw data subjected to preprocessing or convolution by the preprocessing unit 36c, based on the enlargement instruction.

For example, the enlargement reconstructing unit 36d performs the following processing when a region of interest (ROI) 41 as illustrated in the center part in FIG. 4 is set in the CT image 40 illustrated in the left part in FIG. 4 and an enlargement instruction received from the operator is transmitted from the input device 31. Specifically, the enlargement reconstructing unit 36d reconstructs an enlarged CT image serving as a CT image obtained by enlarging the region in the ROI 41 set in the CT image 40, using the raw data stored in the RAM of the preprocessing unit 36c in accordance with enlargement conditions included in the enlargement instruction. Various methods may be used as the reconstruction method, such as back projection. An example of back projection is back projection by FBP. The enlargement conditions include the enlargement ratio and the enlargement center.

Next, the enlargement reconstructing unit 36d subjects the enlarged CT image to noise reduction, beam hardening reduction (beam hardening correction), or the like, as post processing. The enlarged CT image having been subjected to noise reduction and beam hardening reduction is displayed on the display device 32 under the control of the display controlling unit 38a described later. For example, as illustrated in the right part in FIG. 4, an enlarged CT image 42 having been subjected to noise reduction and beam hardening reduction is displayed in a certain display region of the display device 32.

Conventional X-ray CT apparatuses subject raw data to preprocessing or convolution after receiving an enlargement instruction, to reconstruct an enlarged CT image using the raw data having been subjected to preprocessing or convolution. For this reason, conventional X-ray CT apparatuses may fail to promptly reconstruct an enlarged CT image. However, as described above, the X-ray CT apparatus according to the present embodiment reconstructs an enlarged CT image using raw data that have already been subjected to preprocessing or convolution by the preprocessing unit 36c, when the X-ray CT apparatus receives an enlargement instruction. For this reason, the X-ray CT apparatus according to the present embodiment enables prompt reconstruction of an enlarged CT image, because the X-ray CT apparatus does not require preprocessing or convolution after receiving an enlargement instruction.

The image storage 37 stores various image data generated by the image reconstructing unit 36. For example, the image storage 37 stores image data of CT images and image data of enlarged CT images.

The controller 38 includes a display controlling unit 38a. The controller controls operations of the frame device 10, the couch device 20, and the console device 30, to control the whole X-ray CT apparatus. Specifically, the controller 38 controls the scan controller 33 to control scans performed by the frame device 10. The controller 38 also controls the preprocessing unit 34 and the image reconstructing unit 36, to control image reconstruction in the console device 30.

The display controlling unit 38a performs control to cause images indicated by the various image data stored in the image storage 37 to be displayed on the display device 32. For example, the display controlling unit 38a performs control to cause a CT image indicated by image data of the CT image to be displayed in a certain display region of the display device 32, and to cause an enlarged CT image indicated by image data of the enlarged CT image to be displayed in a certain display region of the display device 32.

The above raw data storage 35 and the image storage 37 may be achieved by semiconductor memory devices such as RAMs or flash memories, hard disks, or optical disks. The above scan controller 33, the preprocessing unit 34, the image reconstructing unit 36, and the controller 38 may be achieved with integrated circuits such as application specific integrated circuits (ASIC) and field programmable gate arrays (FPGA), or electronic circuits such as central processing units (CPU) and micro processing units (MPU).

Figure 5:
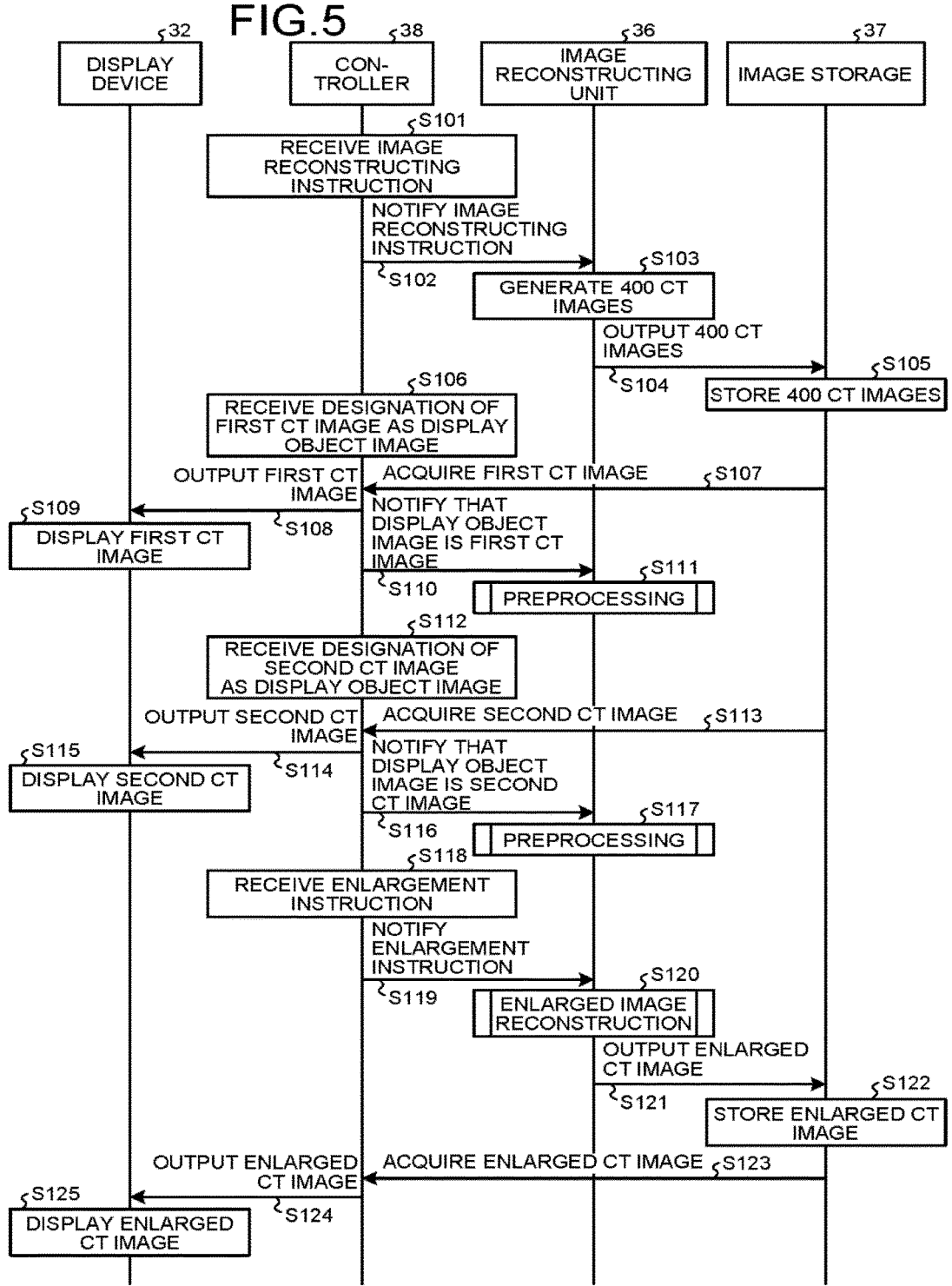
FIG. 5 is a sequence diagram for explaining an example of processing of the X-ray CT apparatus according to the first embodiment.

The whole configuration of the X-ray CT apparatus according to the first embodiment has been explained above. The following is explanation an example of processing performed by the X-ray CT apparatus according to the first embodiment with reference to FIG. 5. FIG. 5 is a sequence diagram for explaining an example of processing performed by the X-ray CT apparatus according to the first embodiment. The sequence diagram illustrated in the example of FIG. 5 indicates processing performed in the case of receiving an enlargement instruction for the second CT image.

As illustrated in FIG. 5, when the controller 38 of the X-ray CT apparatus according to the first embodiment receives an image reconstructing instruction transmitted from the input device 31 (Step S101), the controller 38 notifies the first image reconstructing unit 36a of the image reconstructing unit 36 of the image reconstructing instruction (Step S102).

When the first image reconstructing unit 36a is notified of the image reconstructing instruction, the first image reconstructing unit 36a reconstructs 400 CT images using the raw data stored in the raw data storage 35 to generate 400 CT images (Step S103). Thereafter, the first image reconstructing unit 36a outputs the 400 CT images to the image storage 37 (Step S104).

When the image storage 37 receives the 400 CT images output from the first image reconstructing unit 36a, the image storage 37 stores image data of the received 400 CT images (Step S105).

Thereafter, when the display controlling unit 38a of the controller 38 receives a CT image display instruction (that is, an instruction to display the first CT image) transmitted from the input device 31 and designating the first CT image as the display object image (Step S106), the display controlling unit 38a acquires the first CT image from the image storage 37 (Step S107). The display controlling unit 38a outputs the acquired first CT image to the display device 32 (Step S108).

When the display device 32 receives the first CT image output from the display controlling unit 38a, the display device 32 displays the received first CT image (Step S109).

The controller 38 notifies the preprocessing unit 36c of the image reconstructing unit 36 that the display object image is the first CT image (Step S110). When the preprocessing unit 36c is notified by the controller 38 that the display object image is the first CT image, the preprocessing unit 36c executes preprocessing in accordance with the notified details (Step S111).

Figure 6:
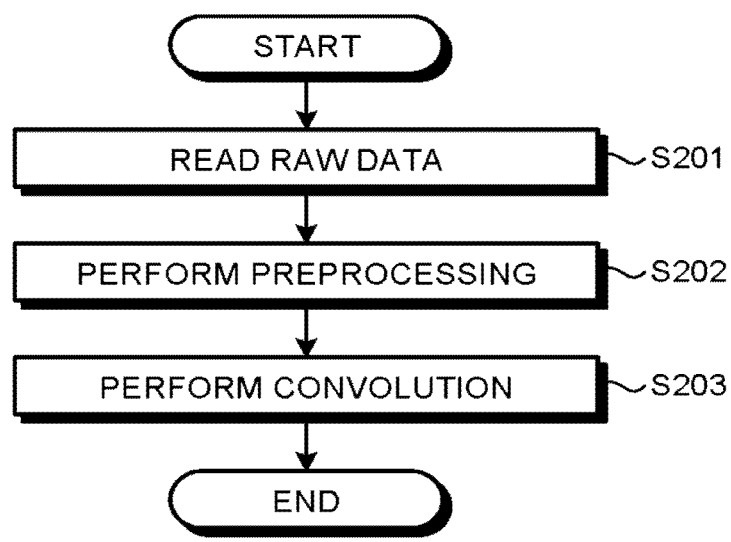
FIG. 6 is a flowchart for explaining an example of preprocessing executed by a preprocessing unit according to the first embodiment.

FIG. 6 is a flowchart for explaining an example of preprocessing executed by the preprocessing unit according to the first embodiment. As illustrated in FIG. 6, the preprocessing unit 36c of the X-ray CT apparatus according to the first embodiment reads the raw data that was used for reconstructing the CT image (first CT image) designated as the display object image from the raw data storage 35 (Step 3201).

The preprocessing unit 36c preprocesses the read raw data (Step S202). Next, the preprocessing unit 36c performs convolution on the preprocessed raw data (S203), and ends the preprocessing.

With reference to FIG. 5 again, thereafter, when the display controlling unit 38a of the controller 38 receives a CT image display instruction (that is, an instruction to display the second CT image) transmitted from the input device 31 and designating the second CT image as the display object image (Step S112), the display controlling unit 38a acquires the second CT image from the image storage 37 (Step S113). The display controlling unit 38a outputs the acquired second CT image to the display device 32 (Step S114).

When the display device 32 receives the second CT image output from the display controlling unit 38a, the display device 32 displays the received second CT image (Step S115).

The controller 38 notifies the preprocessing unit 36c of the image reconstructing unit 36 that the display object image is the second CT image (Step S116). When the preprocessing unit 36c is notified by the controller 38 that the display object image is the second CT image, the preprocessing unit 36c executes preprocessing in accordance with the notified details (Step S117).

In the preprocessing in Step S117, first, the preprocessing unit 36c reads the raw data that was used for reconstructing the CT image (second CT image) designated as the display object image from the raw data storage 35. Thereafter, the preprocessing unit 36c preprocesses the read raw data. The preprocessing unit 36c performs convolution on the preprocessed raw data. These processes are performed in the preprocessing in Step S117.

When an ROI is set for the second CT image displayed on the display device 32 and the controller 38 receives an enlargement instruction transmitted from the input device 31 (Step S118), the controller 38 notifies the enlargement reconstructing unit 36d of the image reconstructing unit 36 of the enlargement instruction for the second CT image (Step S119).

When the enlargement reconstructing unit 36d is notified of the enlargement instruction for the second CT image by the controller 38, the enlargement reconstructing unit 36d executes enlarged image reconstruction in accordance with the contents of the notified enlargement instruction (Step S120).

Figure 7:
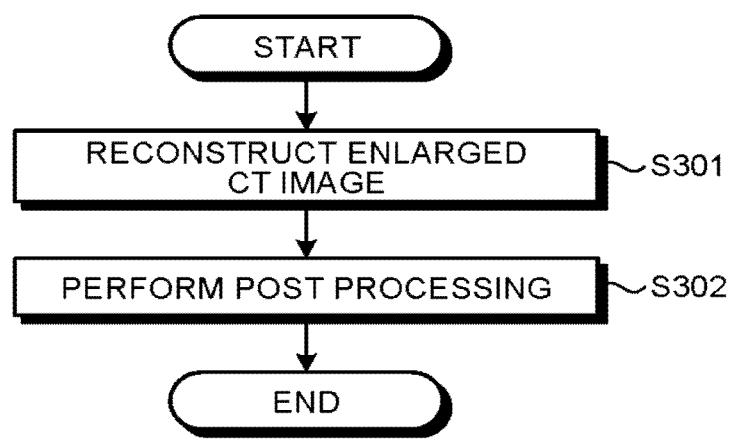
FIG. 7 is a flowchart for explaining an example of enlarged image reconstruction executed by an enlargement reconstructing unit according to the first embodiment.

FIG. 7 is a flowchart for explaining an example of enlarged image reconstruction executed by the enlargement reconstructing unit according to the first embodiment. As illustrated in FIG. 7, the enlargement reconstructing unit 36d reconstructs an enlarged CT image serving as a CT image obtained by enlarging the region in the ROI using the raw data stored in the RAM of the preprocessing unit 36c, in accordance with the enlargement conditions included in the enlargement instruction (Step S301).

The enlargement reconstructing unit 36d subjects the enlarged CT image to noise reduction and beam hardening reduction (Step S302) as post processing, and ends the enlarged image reconstruction.

With reference to FIG. 5 again, the enlargement reconstructing unit 36d outputs the enlarged CT image having been subjected to noise reduction and beam hardening reduction to the image storage 37 (Step S121).

When the image storage 37 receives the enlarged CT image output from the enlargement reconstructing unit 36d, the image storage 37 stores image data of the received enlarged CT image (Step S122).

Next, the display controlling unit 38a of the controller 38 acquires the enlarged CT image from the image storage 37 (Step S123). The display controlling unit 38a outputs the acquired enlarged CT image to the display device 32 (Step S124).

When the display device 32 receives the enlarged CT image output from the display controlling unit 38a, the display device 32 displays the received enlarged CT image (Step S125).

The X-ray CT apparatus according to the first embodiment has been explained above. As described above, the X-ray CT apparatus according to the first embodiment enables prompt reconstruction of an enlarged CT image, because the X-ray CT apparatus does not require preprocessing or convolution after receiving an enlargement instruction.

First Modification According to the First Embodiment

The first embodiment described above illustrates an example in which the display controlling unit 38a waits for completion of reconstruction of an enlarged CT image, to perform control to cause the reconstructed enlarged CT image to be displayed on the display device 32, when the input device 31 transmits an enlargement instruction received from the operator to the controller 38. However, the display controlling unit 38a may cause the CT image designated as the display object image to be displayed in an enlarged state in a certain display region of the display device 32 to display the enlarged CT image, during the time from reception of an enlargement instruction to completion of reconstruction of the enlarged CT image. Such an embodiment will be explained hereinafter with reference to FIG. 8, as a first modification of the first embodiment.

Figure 8:
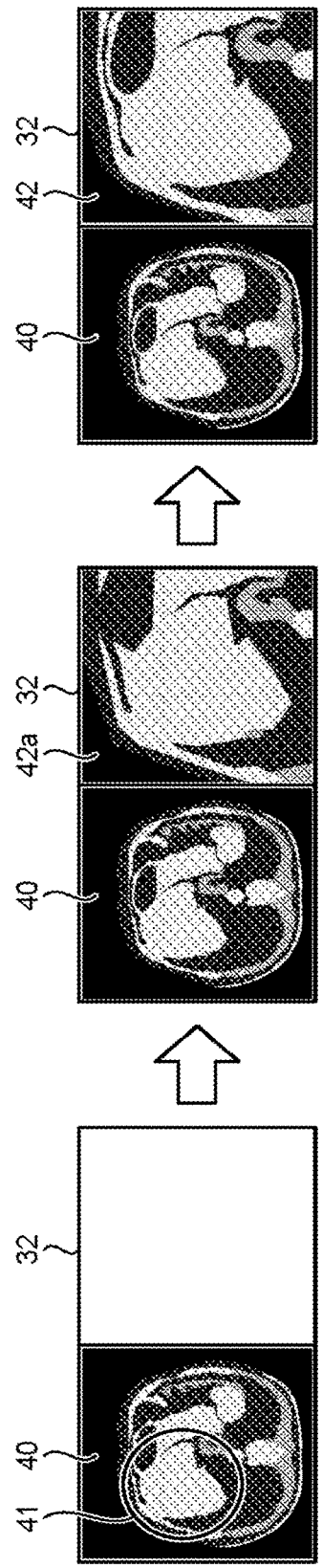
FIG. 8 is a diagram for explaining a first modification according to the first embodiment.

FIG. 8 is a diagram for explaining the first modification of the first embodiment. In the first modification, as illustrated in the left part in FIG. 8, when the ROI 41 is set for the CT image 40 displayed in a certain display region of the display device 32 and an enlargement instruction received from the operator is transmitted from the input device 31 to the controller 38, the enlargement reconstructing unit 36d reconstructs an enlarged CT image as described above. However, reconstruction of an enlarged CT image requires much time. For this reason, the operator feels stressed if an enlarged CT image is displayed on the display device 32 after completion of reconstruction, waiting for completion of reconstruction of the enlarged CT image. For this reason, the display controlling unit 38a according to the first modification generates an enlarged CT image 42a obtained by enlarging the reconstructed CT image designated as the display object image. The display controlling unit 38a according to the first modification displays the CT image 42a in a certain display region of the display device 32 to display the enlarged CT image, until reconstruction of the enlarged CT image is completed after receiving the enlargement instruction, as illustrated in the center part in FIG. 8. The CT image 42a has inferior resolution to that of the enlarged CT image 42 obtained by newly reconstructing the CT image. After the enlargement reconstructing unit 36d completes reconstruction of the enlarged CT image, the display controlling unit 38a according to the first modification performs control to display the enlarged CT image 42 in a certain display region of the display device 32, as illustrated in the right part in FIG. 8. This configuration reduces the operator's stress caused by time lag from input of the enlargement instruction to display of the enlarged CT image 42 on the display device 32.

Second Modification According to the First Embodiment

The first embodiment described above illustrates the case where the preprocessing unit 36c performs preprocessing on raw data corresponding to the CT image designated as the display object image, every time any of a plurality of CT images is designated as the display object image. However, the preprocessing unit 36c may perform preprocessing on raw data corresponding to a plurality of CT images including the CT image designated as the display object image, every time any of the CT images is designated as the display object image. Such an embodiment will be explained hereinafter as a second modification according to the first embodiment, with reference to FIG. 9.

Figure 9:
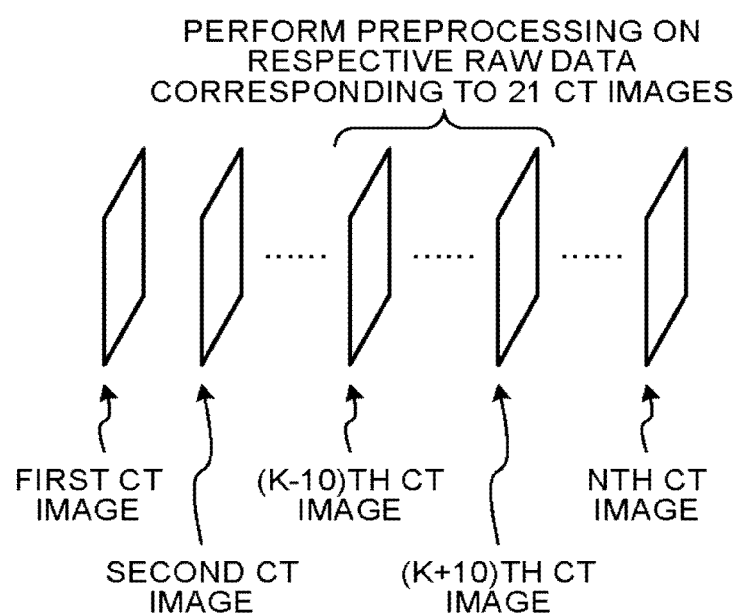
FIG. 9 is a diagram for explaining a second modification according to the first embodiment.

FIG. 9 is a diagram for explaining the second modification according to the first embodiment. In the second modification, for example, when a $K^{th}$ (K is a natural number) CT image is designated as the display object image, first, the preprocessing unit 36c performs preprocessing or convolution on raw data corresponding to the $K^{th}$ CT image. Next, the preprocessing unit 36c successively performs preprocessing or convolution on raw data corresponding to the other CT images than the $K^{th}$ CT image until another new CT image is designated as the display object image. For example, the preprocessing unit 36c performs preprocessing or convolution on raw data corresponding to $(K-1)^{th}$, $(K+1)^{th}$, $(K-2)^{th}$, $(K+2)^{th}$, . . . , $(K-L)^{th}$, and $(K+L)^{th}$ CT images. L is a natural number. For example, FIG. 9 illustrates an example where the preprocessing unit 36c performs preprocessing or convolution on raw data corresponding to $(K-10)^{th}$ to $(K+10)^{th}$ CT images (21 CT images).

Thereafter, the preprocessing unit 36c stores the raw data having been subjected to preprocessing or convolution in the RAM. Next, when another new CT image is designated as the display object image, the preprocessing unit 36c does not perform preprocessing or convolution on the raw data corresponding to the other CT images, in the case where the raw data corresponding to the other preprocessed or convoluted CT images have already been stored in the RAM. In this manner, the second modification enables reduction in the processing load when another new CT image is designated as the display object image, by preprocessing a plurality of raw data corresponding to a plurality of CT images when a CT image is designated as the display object image.

Second Embodiment

The following is explanation of the X-ray CT apparatus according to a second embodiment. Explanation of constituent elements similar to those of the first embodiment may be omitted with the same reference numerals assigned. The X-ray CT apparatus according to the second embodiment is different from the X-ray CT apparatus according to the first embodiment, in that the former includes an image reconstructing unit different from the image reconstructing unit 36.

Figure 10:
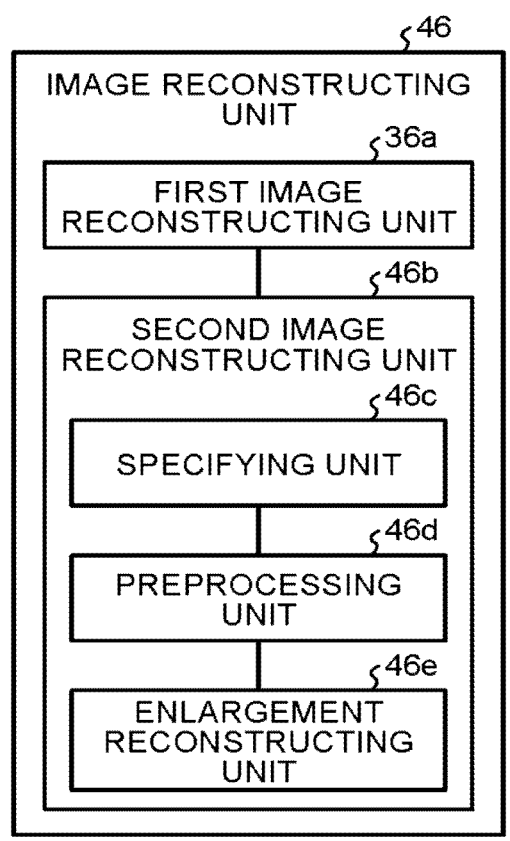
FIG. 10 is a diagram illustrating an example of the configuration of the image reconstructing unit according to a second embodiment.

FIG. 10 is a diagram illustrating an example of the configuration of the image reconstructing unit according the second embodiment. As illustrated in FIG. 10, an image reconstructing unit 46 according to the second embodiment includes the first image reconstructing unit 36a and a second image reconstructing unit 46b. The image reconstructing unit 46 can be achieved with an integrated circuit such as an ASIC and an FPGA, or an electronic circuit such as a CPU and an MPU.

As illustrated in FIG. 10, the second image reconstructing unit 46b includes specifying unit 46c, a preprocessing unit 46d, and an enlargement reconstructing unit 46e.

The specifying unit 46c specifies a CT image including an image indicating a certain legion region among a plurality of CT images reconstructed by the first image reconstructing unit 36a. For example, when a contrast medium is administered to the subject P, a part having a CT value equal to or higher than a predetermined threshold in the CT image is estimated as an image indicating a lesion region such as a bleeding region or a tumor region. For this reason, the specifying unit 46c determines whether the CT image includes any part having a CT value equal to or larger than a predetermined threshold, for each of the CT images. The specifying unit 46c specifies the CT image determined as including a part having a CT value equal to or larger than a predetermined threshold, as a CT image including an image indicating a certain lesion region.

The preprocessing unit 46d preprocesses the raw data corresponding to the CT image specified by the specifying unit 46c.

For example, the preprocessing unit 46d reads raw data that was used for reconstructing the CT image specified by the specifying unit 46c from the raw data storage 35. When the raw data was read out, the preprocessing unit 46d subjects the read raw data to preprocessing similar to the preprocessing performed by the preprocessing unit 36c in the first embodiment.

Thereafter, the preprocessing unit 46d subjects the preprocessed raw data to convolution to reduce blurredness of the image. The preprocessing unit 46d may omit convolution, performing only preprocessing on the raw data.

The preprocessing unit 46d stores the preprocessed or convoluted raw data in the RAM included in the preprocessing unit 46d. Specifically, the present embodiment stores, in the RAM, raw data corresponding to the CT image that includes an image indicating a certain lesion region and is probably designated as an object of an enlargement instruction after the raw data has already been subjected to preprocessing or convolution.

When the enlargement reconstructing unit 46e receives an enlargement instruction, the enlargement reconstructing unit 46e reconstructs an enlarged CT image using raw data having been preprocessed or convoluted by the preprocessing unit 46d, based on the enlargement instruction.

For example, when the enlargement reconstructing unit 46e is notified of an enlargement instruction for the CT image displayed on the display device 32 from the controller 38, the enlargement reconstructing unit 46e performs the following processing, in the case where raw data corresponding to the CT image displayed on the display device 32 is stored in the RAM. Specifically, the enlargement reconstructing unit 46e reconstructs an enlarged CT image serving as a CT image obtained by enlarging the region in the ROI that is set in the displayed CT image, using the raw data corresponding to the CT image displayed on the display device 32 among the raw data stored in the RAM of the preprocessing unit 46d, in accordance with the enlargement conditions included in the enlargement instruction.

When no raw data corresponding to the displayed CT image is stored in the RAM, the enlargement reconstructing unit 46e reads the raw data that was used for reconstructing the displayed CT image from the raw data storage 35. The enlargement reconstructing unit 46e subjects the read raw data to preprocessing similar to the preprocessing performed by the preprocessing unit 36c in the first embodiment. Thereafter, the enlargement reconstructing unit 46e subjects the preprocessed raw data to convolution. The enlargement reconstructing unit 46e may omit convolution, performing only preprocessing on the raw data. The enlargement reconstructing unit 46e reconstructs an enlarged CT image using the preprocessed or convoluted raw data, based on an enlargement instruction. Thereafter, the enlargement reconstructing unit 46e subjects the enlarged CT image to noise reduction and beam hardening reduction as post processing.

Figure 11:
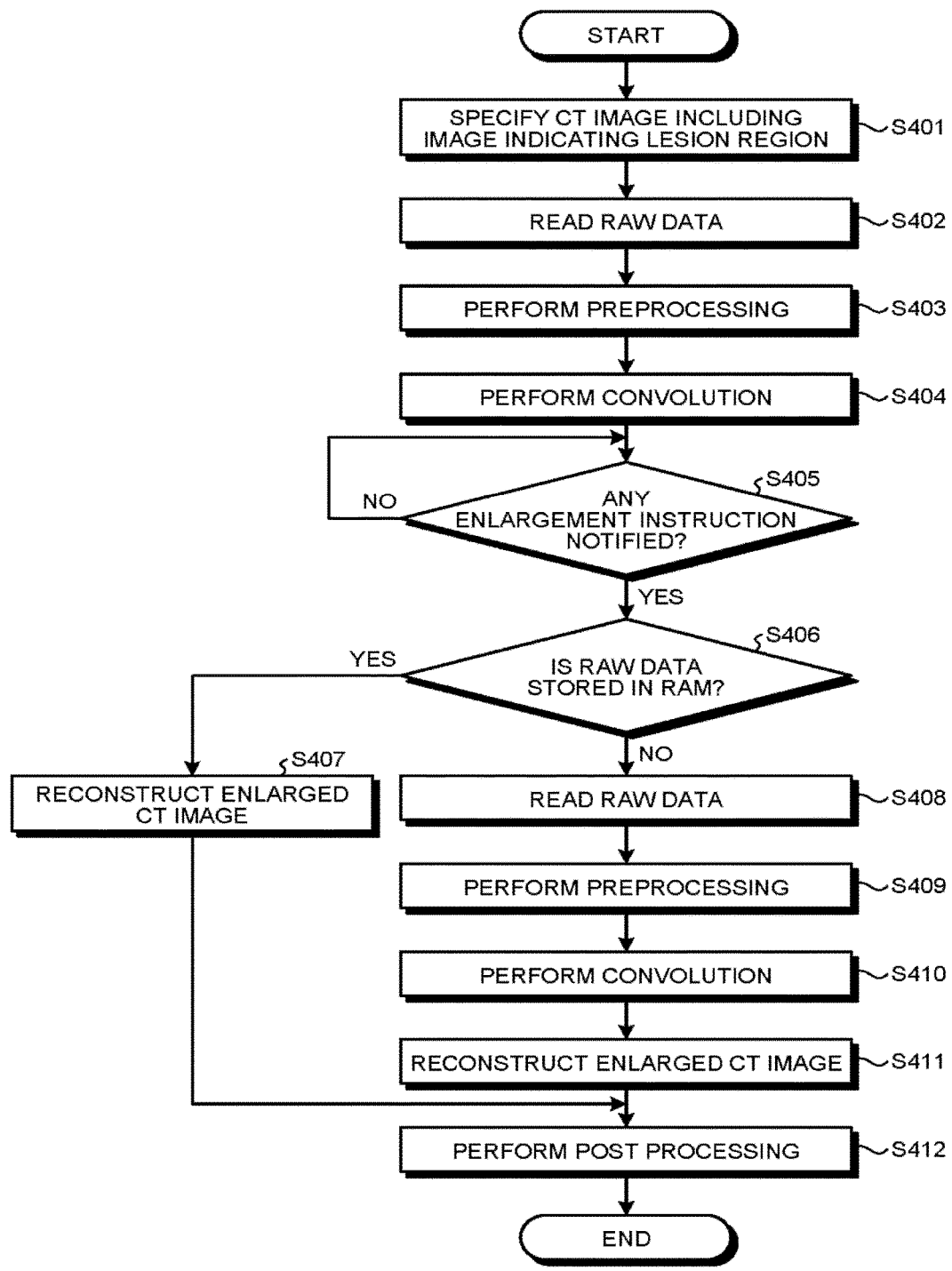
FIG. 11 is a flowchart for explaining an example of processing of the X-ray CT apparatus according to the second embodiment.

The following is explanation of an example of enlarged image reconstruction executed by the second image reconstructing unit 46b of the X-ray CT apparatus according to the second embodiment, with reference to FIG. 11. The enlarged image reconstruction is executed when the input device 31 transmits an instruction that was received from the operator to execute enlarged image reconstruction to the controller 38, in the state where the image storage 37 stores a plurality of reconstructed CT images. FIG. 11 is a flowchart for explaining an example of the enlarged image reconstruction executed by the second image reconstructing unit 46b according to the second embodiment.

As illustrated in FIG. 11, the specifying unit 46c of the X-ray CT apparatus according to the second embodiment specifies a CT image including an image indicating a certain lesion region among the CT images reconstructed by the first image reconstructing unit 36a (Step S401).

Thereafter, the preprocessing unit 46d reads raw data that was used for reconstructing the CT image specified by the specifying unit 46c from the raw data storage 35 (Step S402). The preprocessing unit 46d preprocesses the read raw data (Step S403).

The preprocessing unit 46d subjects the preprocessed raw data to convolution to reduce blurredness of the image, and to store the convoluted raw data in the RAM of the preprocessing unit 46d (Step S404). Thereafter, the enlargement reconstructing unit 46e determines whether any enlargement instruction for the CT image displayed on the display device 32 was notified from the controller 38 (Step S405). When the enlargement reconstructing unit 46e determines that no enlargement instruction was notified from the controller 38 (Step S405; No), the enlargement reconstructing unit 46e performs determination of Step S405 again.

By contrast, when the enlargement reconstructing unit 46e determines that an enlargement instruction was notified from the controller 38 (Step S405; Yes), the enlargement reconstructing unit 46e determines whether any preprocessed or convoluted raw data corresponding to the CT image displayed on the display device 32 is stored in the RAM of the preprocessing unit 46d (Step S406).

When the enlargement reconstructing unit 46e determines that raw data corresponding to the displayed CT image is stored in the RAM (Step S406; Yes), the enlargement reconstructing unit 46e performs the following processing. Specifically, the enlargement reconstructing unit 46e reconstructs an enlarged CT image serving as a CT image obtained by enlarging the region in the ROT that is set in the displayed CT image, using the raw data corresponding to the CT image displayed on the display device 32 among the raw data stored in the RAM, in accordance with enlargement conditions included in the enlargement instruction (Step S407), and goes to Step S412 described later.

By contrast, when the enlargement reconstructing unit 46e determines that no raw data corresponding to the displayed CT image is stored in the RAM (Step S406; No), the enlargement reconstructing unit 46e reads the raw data that was used for reconstructing the displayed CT image from the raw data storage 35 (Step S406). The enlargement reconstructing unit 46e preprocesses the read raw data (Step S409). The enlargement reconstructing unit 46e subjects the preprocessed raw data to convolution (Step S410). The enlargement reconstructing unit 46e reconstructs an enlarged CT image serving as a CT image obtained by enlarging the region in the ROI that is set in the displayed CT image, using the preprocessed or convoluted raw data, in accordance with enlargement conditions included in the enlargement instruction (Step S411). Thereafter, the enlargement reconstructing unit 46e subjects the enlarged CT image to noise reduction and beam hardening reduction as post processing (Step S412), and ends the enlarged image reconstruction.

The X-ray CT apparatus according to the second embodiment has been explained above. The X-ray CT apparatus according to the second embodiment reconstructs an enlarged CT image using raw data that is stored in the RAM and has already been preprocessed or convoluted, in the case where the raw data corresponding to the CT image to be enlarged is stored in the RAM when an enlargement instruction is received. The X-ray CT apparatus according to the second embodiment having the above configuration enables prompt reconstruction of an enlarged CT image when raw data corresponding to the CT image to be enlarged is stored in the RAM, because the X-ray CT apparatus does not require preprocessing or convolution after receiving an enlargement instruction.

Third Embodiment

An image processing apparatus connected with the X-ray CT apparatus via a network may be provided with the functions of the X-ray CT apparatus according to the first embodiment or the functions of the X-ray CT apparatus according to the second embodiment. Such an embodiment will be explained hereinafter as a third embodiment with reference to FIG. 12.

Figure 12:
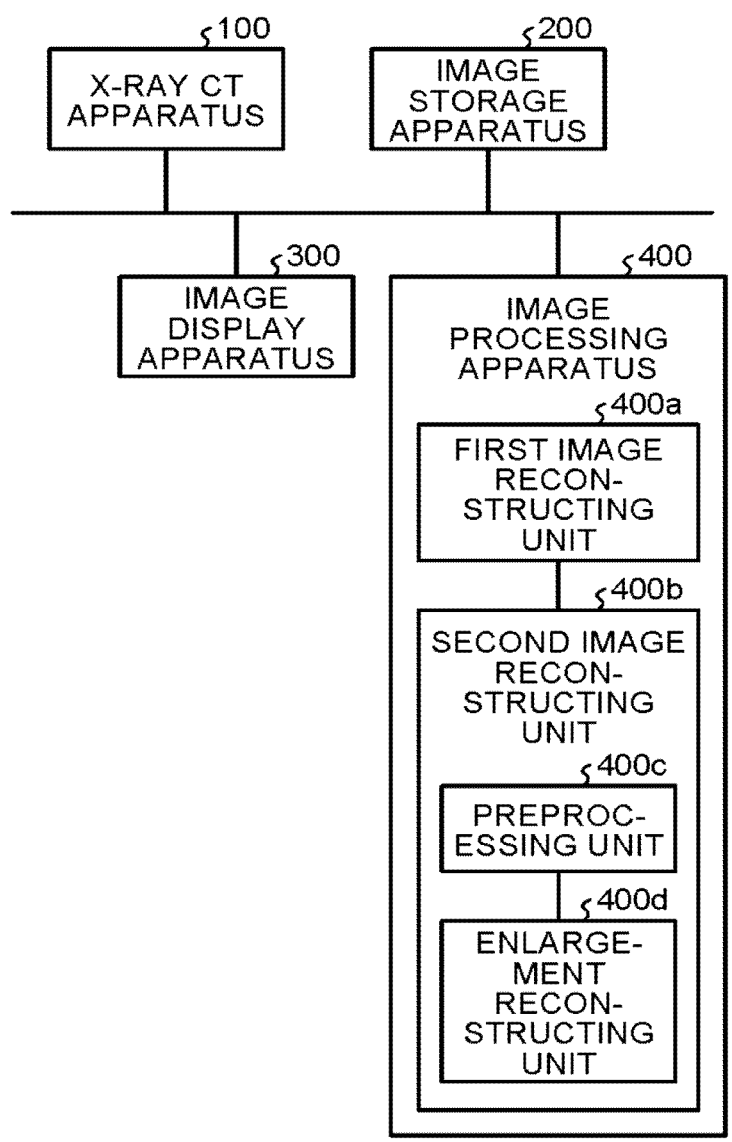
FIG. 12 is a diagram for explaining a third embodiment.

FIG. 12 is a diagram for explaining the third embodiment. The system illustrated in the example of FIG. 12 includes an X-ray CT apparatus 100, an image storage apparatus 200, an image display apparatus 300, and an image processing apparatus 400. The X-ray CT apparatus 100, the image storage apparatus 200, the image display apparatus 300, and an image processing apparatus 400 can mutually communicate with each other directly or indirectly, for example, via an in-hospital local area network (LAN) installed in the hospital. For example, when a picture archiving and communication system (PACS) has been introduced, the apparatuses 100 to 400 mutually transmit and receive images and the like, in conformity with the digital imaging and communications in medicine (DICOM).

The X-ray CT apparatus 100 is an X-ray CT apparatus according to the first embodiment, or an X-ray CT apparatus according to the second embodiment. For example, the X-ray CT apparatus 100 transmits raw data to the image processing apparatus 400.

The image storage apparatus 200 is a database that stores CT images and enlarged CT images reconstructed by the X-ray CT apparatus 100 and the image processing apparatus 400.

The image display apparatus 300 is a monitor or a play that displays CT image and enlarged CT images stored in the image storage apparatus 200.

The image processing apparatus 400 is a workstation having functions equivalent to the functions of the X-ray CT apparatus according to the first embodiment, the functions of the X-ray CT apparatus according to the second embodiment, or the functions of the X-ray CT apparatus according to a fourth embodiment described later. The image processing apparatus 400 executes processing similar to the processing executed by the X-ray CT apparatus according to the first embodiment, the X-ray CT apparatus according to the second embodiment, or the X-ray CT apparatus according to the fourth embodiment described later, using the CT images stored in the image storage apparatus 200 and the raw data transmitted from the X-ray CT apparatus 100.

For example, as illustrated in FIG. 12, when the image processing apparatus 400 has functions equivalent to the functions of the X-ray CT apparatus according to the first embodiment, the image processing apparatus 400 includes a first image reconstructing unit 400a, and a second image reconstructing unit 400b. The second image reconstructing unit 400b includes a preprocessing unit 400c and an enlargement reconstructing unit 400d. The functions exhibited by the first image reconstructing unit 400a are equivalent to the functions exhibited by the first image reconstructing unit 36a according to the first embodiment. The functions exhibited by the second image reconstructing unit 400b are equivalent to the functions exhibited by the second image reconstructing unit 36b according to the first embodiment. The functions exhibited by the preprocessing unit 400c are equivalent to the functions exhibited by the preprocessing unit 36c according to the first embodiment. The functions exhibited by the enlargement reconstructing unit 400d are equivalent to the functions exhibited by the enlargement reconstructing unit 36d according to the first embodiment.

The image processing apparatus 400 according to the third embodiment described above enables prompt reconstruction of an enlarged CT image, because the image processing apparatus 400 has functions equivalent to the functions of the X-ray CT apparatus according to the first embodiment, or the functions of the X-ray CT apparatus according to the second embodiment.

Fourth Embodiment

The first embodiment described above illustrates the case of performing preprocessing on raw data corresponding to the CT image designated as the display object image, every time any of a plurality of CT images is designated as the display object image. The second embodiment described above illustrates the case of performing preprocessing on raw data corresponding to the specified CT image, when the specifying unit 46c specifies a CT image including an image indicating a certain lesion region among a plurality of CT images. However, the X-ray CT apparatus may perform the following first initialization, second initialization, and third initialization, in addition to the preprocessing, every time any of a plurality of CT images is designated as the display object image. In addition, the X-ray CT apparatus may perform the following first initialization, second initialization, and third initialization, in addition to the preprocessing, when a CT image including an image indicating a certain lesion region is specified among a plurality of CT images. Such an embodiment will be explained hereinafter as the fourth embodiment. In the fourth embodiment, explanation of constituent elements similar to those in the first embodiment and the second embodiment may be omitted with the same reference numerals attached.

The following is explanation of a method for performing the following first initialization, the second initialization, and the third initialization by the X-ray CT apparatus in addition to the preprocessing, every time any of a plurality of CT images is designated as the display object image. However, any method similar to the method explained hereinafter may be used to perform the following first initialization, the second initialization, and the third initialization in addition to the preprocessing, when the specifying unit 46c specifies a CT image including an image indicating a certain lesion region.

The X-ray CT apparatus according to the fourth embodiment is different from the X-ray CT apparatus according to the first embodiment, in that the X-ray CT apparatus according to the fourth embodiment includes an image reconstructing unit that is different from the image reconstructing unit 36.

Figure 13:
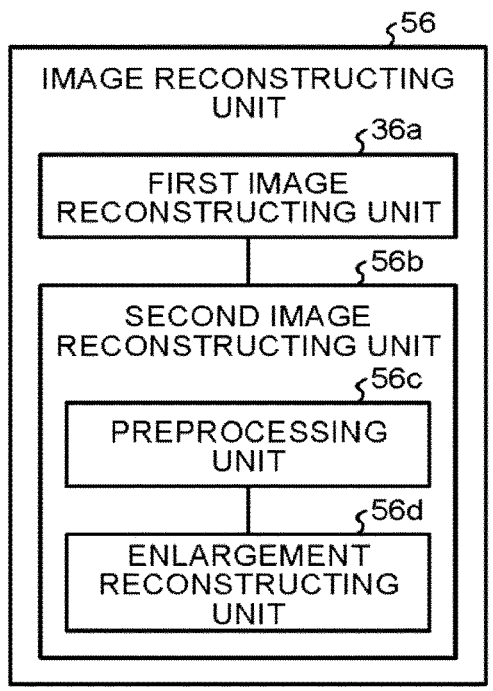
FIG. 13 is a diagram illustrating an example of the configuration of the image reconstructing unit according to a fourth embodiment.

FIG. 13 is a diagram illustrating an example of the configuration of the image reconstructing unit according to the fourth embodiment. As illustrated in FIG. 13, an image reconstructing unit 56 according to the fourth embodiment includes the fire image reconstructing unit 36a, and a second image reconstructing unit 56b. The image reconstructing unit 56 can be achieved with an integrated circuit such as an ASIC and an FPGA, or an electronic circuit such as a CPU and an MPU.

The second image reconstructing unit 56b performs first initialization, every time any of the CT images reconstructed by the first image reconstructing unit 36a is designated as the display object image. The first initialization includes processing of starting up real-time process to execute preprocessing and enlarged image reconstruction. When the second image reconstructing unit 56b that has started up the real-time process to execute preprocessing and enlarged image reconstruction is functionally illustrated, the second image reconstructing unit 56b includes a preprocessing unit 56c and an enlargement reconstructing unit 56d, as illustrated in FIG. 13.

The preprocessing unit 56c performs the following processing, in addition to the above processing executed by the preprocessing unit 36c according to the first embodiment. Specifically, the preprocessing unit 56c performs second initialization, every time any of the CT images reconstructed by the first image reconstructing unit 36a is designated as the display object image.

The second initialization includes processing of reading parameters from a parameter table that records parameters to be used in the software corresponding to the preprocessing unit 56c. The second initialization also includes processing of securing a storage area of the RAM that temporarily stores data to be used in the processing executed by the preprocessing unit 56c. The second initialization also includes processing of reading raw data that was used for reconstructing the CT image designated as the display object image from the raw data storage 35.

The enlargement reconstructing unit 56d executes the following processing, in addition to the above processes executed by the enlargement reconstructing unit 56d according to the first embodiment. Specifically, the enlargement reconstructing unit 56d performs the third initialization, every time any of the CT images reconstructed by the first image reconstructing unit 36a is designated as the display object image.

The third initialization includes processing of reading parameters from a parameter table that records parameters to be used in the software corresponding to the enlargement reconstructing unit 56d. The second initialization also includes processing of securing a storage area of the RAM that temporarily stores data to be used in the processing executed by the enlargement reconstructing unit 56d.

The first initialization, the second initialization, and the third initialization are examples of initialization in the claims.

Figure 14:
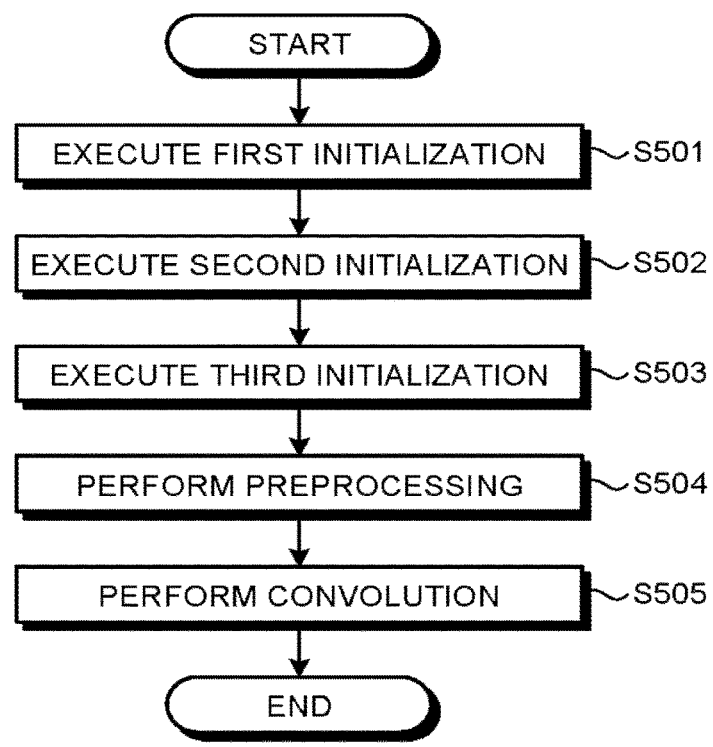
FIG. 14 is a flowchart for explaining an example of preprocessing executed in Step S111 illustrated in the sequence diagram in FIG. 5 in the X-ray CT apparatus according to the fourth embodiment.

FIG. 14 is a flowchart for explaining an example of the processing executed in Step S111 illustrated in the sequence diagram of FIG. 5 above.

As illustrated in FIG. 14, the second image reconstructing unit 56b of the X-ray CT apparatus according to the fourth embodiment executes the first initialization (Step S501). Thereafter, the preprocessing unit 56c executes the second initialization (Step S502). The enlargement reconstructing unit 56d executes the third initialization (Step S503).

The preprocessing unit 56c performs preprocessing on the raw data read by the second initialization (Step S504). The preprocessing unit 56c performs convolution on the preprocessed raw data (S505), to end the processing.

The X-ray CT apparatus according to the fourth embodiment described above executes the first initialization, the second initialization, the third initialization, preprocessing, and convolution before reception of an enlargement instruction. The X-ray CT apparatus according to the present embodiment enables prompt reconstruction of an enlarged CT image, because the apparatus does not require the first initialization, the second initialization, the third initialization, preprocessing or convolution after reception of an enlargement instruction.

Modification of Configuration of X-Ray CT Apparatus

Figure 15:
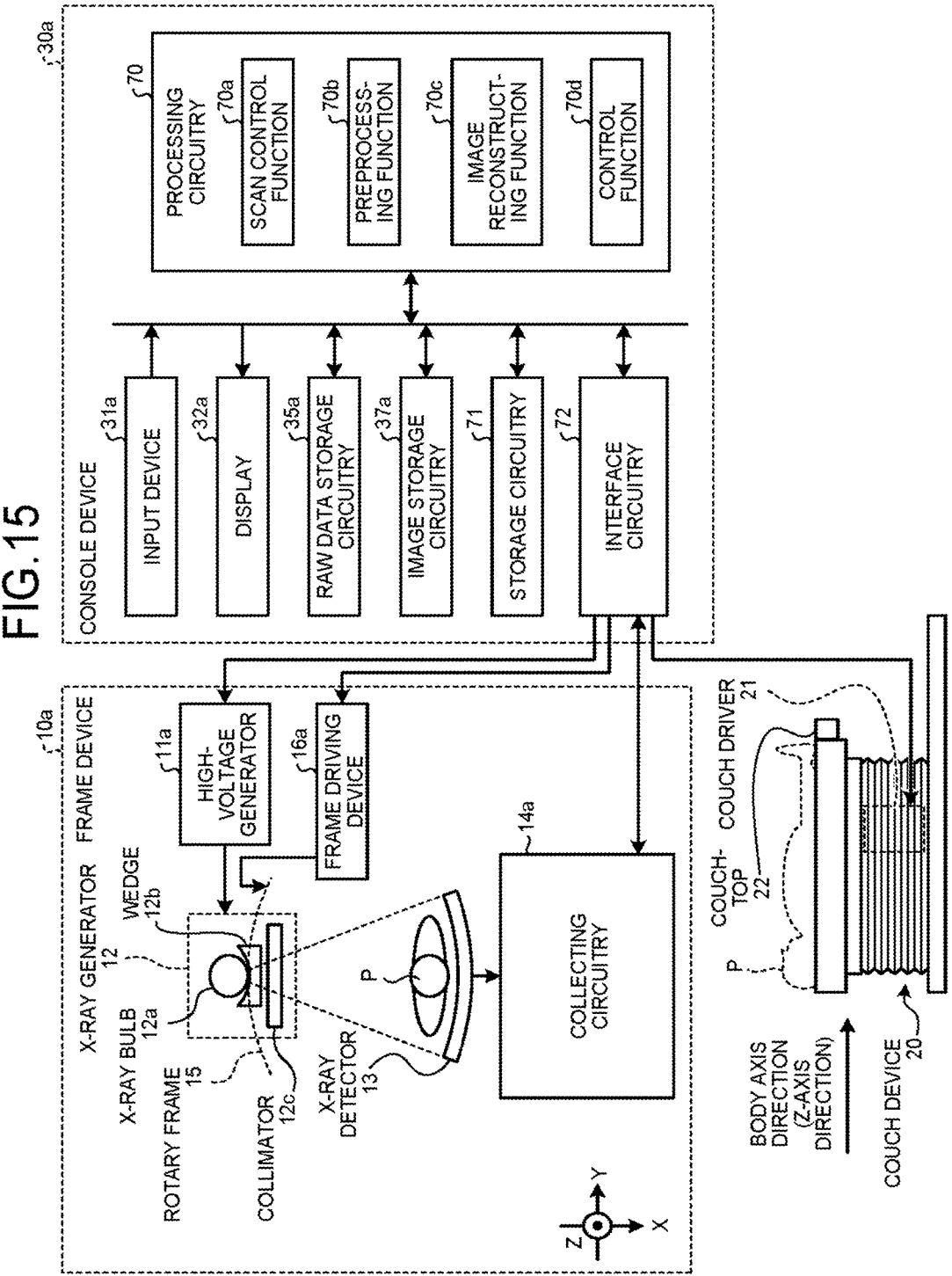
FIG. 15 is a diagram illustrating a configuration example of the X-ray CT apparatus according to a modification.

The X-ray CT apparatus according to the first embodiment, the second embodiment, and the fourth embodiment may have a configuration as illustrated in FIG. 15. FIG. 15 is a diagram illustrating a configuration example of the X-ray CT apparatus according to a modification. Explanation of constituent elements similar to those in the above embodiments is omitted, with reference numerals similar to those attached in the above embodiments. The X-ray CT apparatus according to the modification includes a frame device 10a, the couch device 20, and a console device 30a, as illustrated in FIG. 15.

The frame device 10a applies X-rays to the subject P, to collect projection data from detection data of the X-rays having passed through the subject P. The frame device 10a includes a high-voltage generator 11a, the X-ray generator 12, the X-ray detector 13, collecting circuitry 14a, the rotary frame 15, and a frame driving device 16a.

The high-voltage generator 11a is connected to the X-ray bulb 12a of the X-ray generator 12. The high-voltage generator 11a supplies a bulb voltage or a bulb current to the X-ray bulb 12a. The high-voltage generator 11a regulates the bulb voltage or the bulb current supplied to the X-ray bulb 12a, to regulate the X-ray dose to be applied to the subject F. The high-voltage generator 11a also regulates the aperture of the collimator 12c to regulate the irradiation range of the X-rays.

The frame driving device 16a rotates and drives the rotary frame 15, to revolve the X-ray generator 12 and the X-ray detector 13 on the circular track with the subject P serving as the center. The frame driving device 16a includes, for example, a motor, an electronic circuit, and a driving mechanism. The motor generates motive power to rotate the rotary frame 15. The electronic circuit controls operation of the motor. The driving mechanism converts the motive power generated by the motor into motive power to rotate the rotary frame 15. For example, the driving mechanism is formed of a combination a gear, a belt, a shaft, a bearing and the like.

The rotary frame 15 rotates the X-ray bulb 12a and the X-ray detector 13 in cooperation with the frame driving device 16a.

The collecting circuitry 14a is a DAS having functions similar to the functions of the collector 14 described in the above embodiments. The collecting circuitry 14a is connected to the console device 30a. The collecting circuitry 14a generates projection data, and transmits the generated projection data to the console device 30a.

The console device 30a includes input circuitry 31a, a display 32a, raw data storage circuitry 35a, image storage circuitry 37a, processing circuitry 70, storage circuitry 71, and interface circuitry 72.

The input circuitry 31a, the display 32a, the raw data storage circuitry 35a, the image storage circuitry 37a, the processing circuitry 70, the storage circuitry 71, and the interface circuitry 72 are connected with each other.

The input circuitry 31a is achieved by, for example, a mouse, a keyboard, a button, or a pedal that is used by the operator of the X-ray CT apparatus for inputting various instructions and settings. The input circuitry 31a converts the various instructions and settings input by the operator into electrical signals indicating the various instructions and settings, to output the electrical signals indicating the various instructions and settings to the processing circuitry 70. The input circuitry 31a has functions similar to those of the input device 31 described above.

The display 32a performs various image processing based on the electrical signal received from the processing circuitry 70, and displays various images such as CT images, enlarged CT images, and GUI to receive various settings from the operator via the input circuitry 31a. The display 32a is, for example, a liquid crystal display, or an organic electroluminescence (EL) display. The display 32a has functions similar to the functions of the display device 32 described above.

The raw data storage circuitry 35a stores raw data generated by a preprocessing function 70b described later. The raw data storage circuitry 35a has functions similar to the functions of the raw data storage 35 described above. The raw data storage circuitry 35a is achieved by, for example, a semiconductor memory device such as a RAM or a flash memory, a hard disk, or an optical disk.

The image storage circuitry 37a stores various image data generated by an image reconstructing function 70c described later. For example, the image storage circuitry 37a stores image data of CT images and image data of enlarged CT images. The image storage circuitry 37a has functions similar to the functions of the image storage 37 described above. The image storage circuitry 37a is achieved by, for example, a semiconductor memory device such as a RAM or a flash memory, a hard disk, or an optical disk.

The storage circuitry 71 stores programs to achieve functions of a scan control function 70a, a preprocessing function 70b, the image reconstructing function 70c, and control function 70d. The storage circuitry 71 is achieved by, for example, a semiconductor memory device such as a RAM or a flash memory, a hard disk, or an optical disk.

The raw data storage circuitry 35a, the image storage circuitry 37a, and the storage circuitry 71 may be integrated into one storage circuitry.

The processing circuitry 70 is achieved by, for example, a processor. The processing circuitry 70 reads the program corresponding to the scan control function 70a from the storage circuitry 71, and executes the read program, to execute processing similar to the processing executed by the scan controller 33. The processing circuitry 70 reads the program corresponding to the preprocessing function 70b from the storage circuitry 71, and executes the read program, to execute processing similar to the processing executed by the preprocessing unit 34. The processing circuitry 70 also reads the program corresponding to the image reconstructing function 70c from the storage circuitry 71, and executes the read program, to execute processing similar to the processing executed by the image reconstructing unit 36, the image reconstructing unit 46, or the image reconstructing unit 56. The processing circuitry 70 reads the program corresponding to the control function 70d from the storage circuitry 71, and executes the read program, to execute processing similar to the processing executed by the controller 38. The processing circuitry 70 in the modification is an example of the processing circuitry in the claims.

Steps S101, S102, S106 to S108, S110, S112 to S114, S116, S118, S119, S123, and S124 illustrated in FIG. 5 are steps achieved by the processing circuitry 70 by reading the program corresponding to the control function 70d from the storage circuitry 71, and executing the read program. Steps S105, S104, S111, S117, S120, S121, and S124 illustrated in FIG. 5 are steps achieved by the processing circuitry 70 by reading the program corresponding to the image reconstructing function 70c from the storage circuitry 71, and executing the read program.

Steps S201 to S203 illustrated in FIG. 6 are steps achieved by the processing circuitry 70 by reading the program corresponding to the image reconstructing function 70c from the storage circuitry 71, and executing the read program.

Steps S301 and S302 illustrated in FIG. 7 are steps achieved by the processing circuitry 70 by reading the program corresponding to the image reconstructing function 70c from the storage circuitry 71, and executing the read program.

Steps S501 to S505 illustrated in FIG. 14 are steps achieved by the processing circuitry 70 by reading the program corresponding to the image reconstructing function 70c from the storage circuitry 71, and executing the read program.

With reference to FIG. 15 again, the interface circuitry 72 is a network card to perform communications between the frame device 10a and the console device 30a and between the couch device 20 and the console device 30a.

Modification of Configuration of Image Processing Apparatus

Figure 16:
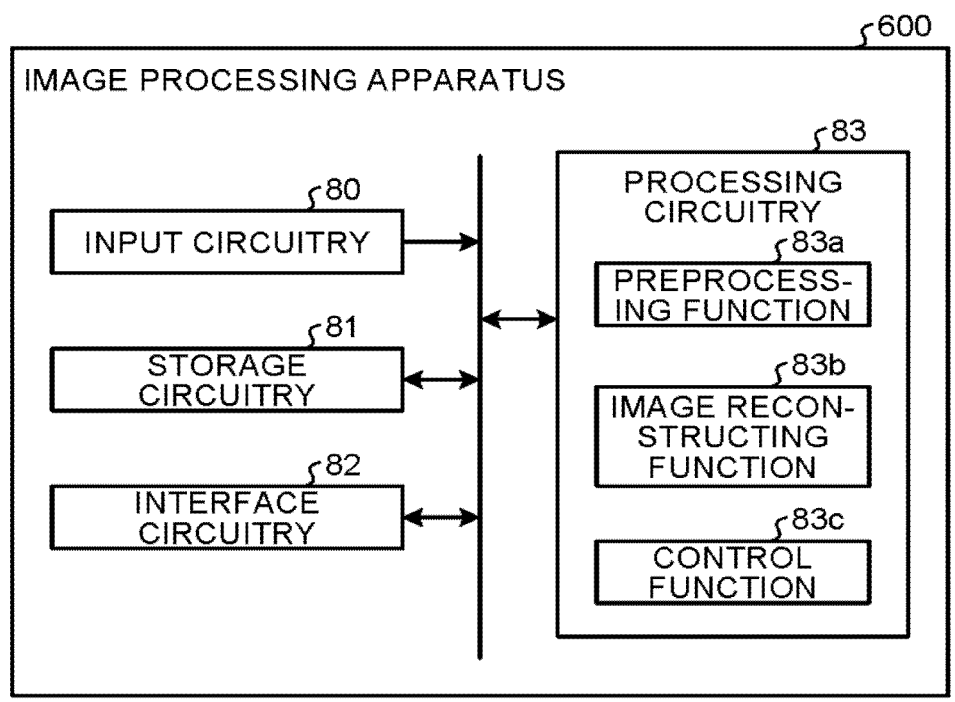
FIG. 16 is a diagram illustrating a configuration example of en image processing apparatus according to a modification.

The image processing apparatus 400 according to the third embodiment may be configured as illustrated in FIG. 16. FIG. 16 is a diagram illustrating a configuration example of the image processing apparatus according to a modification. Explanation of constituent elements similar to those in the above embodiments is omitted, with reference numerals similar to those attached in the above embodiments. An image processing apparatus 600 according to the modification includes input circuitry 80, storage circuitry 81, interface circuitry 82, and processing circuitry 83, as illustrated in FIG. 16.

The input circuitry 80, the storage circuitry 81, the interface circuitry 82, and the processing circuitry 83 are connected with each other.

The input circuitry 80 is achieved by, for example, mouse, a keyboard, a button, or a pedal that is used by the operator for inputting various instructions and settings. The input circuitry 80 converts the various instructions settings input by the operator into electrical signals indicating the various instruction and settings, to output the electrical signals indicating the various instructions and settings to the processing circuitry 83. The input circuitry 80 has functions similar to those of the input device 31 described above.

The storage circuitry 81 stores raw data transmitted from the X-ray CT apparatus 100 illustrated in FIG. 12, by the processing circuitry 83. The storage circuitry 81 also stores various image data generated by an image reconstructing function 83b described later, by the image reconstructing function 83b. For example, the storage circuitry 81 stores image data of CT images and image data of enlarged CT images. Accordingly, the storage circuitry 81 stores raw data, image data CT images and image data of enlarged CT images. The storage circuitry 81 also stores programs to achieve the respective functions of a preprocessing function 83a, the image reconstructing function 83b, and a control function 83c described later. The storage circuitry 81 is achieved by, for example, a semiconductor memory device such as a RAM or a flash memory, a hard disk, and an optical disk.

The interface circuitry 82 is a network card to perform communications between the image processing apparatus 600 and the X-ray CT apparatus 100, the image storage apparatus 200, and the image display apparatus 300.

The processing circuitry 83 is achieved by, for example, a processor. The processing circuitry 83 reads the program corresponding to the preprocessing function 83a from the storage circuitry 81, and executes the read program, to execute processing similar to the processing executed by the preprocessing unit 34 described above. The processing circuitry 83 also reads the program corresponding to the image reconstructing function 83b from the storage circuitry 81, and executes the read program, to execute processing similar to the processing executed by the image reconstructing unit 36, the image reconstructing unit 46, or the image reconstructing unit 56 described above. The processing circuitry 83 also reads the program corresponding to the control function 83c from the storage circuitry 81, and executes the read program, to execute processing similar to the processing executed by the controller 38 described above. The processing circuitry 83 in the modification is an example of the processing circuitry in the claims.

Steps S101, S102, S106 to S108, S110, S112 to S114, S116, S118, S119, S123, and S124 illustrated in FIG. 5 are steps achieved by the processing circuitry 83 by reading the program corresponding to the control function 83c from the storage circuitry 81, and executing the read program. Steps S103, S104, S111, S117, S120, S121, and S124 illustrated in FIG. 5 are steps achieved by the processing circuitry 83 by reading the program corresponding to the image reconstructing function 83b from the storage circuitry 81, and executing the read program.

Steps S201 to S203 illustrated in FIG. 6 are steps achieved by the processing circuitry 83 by reading the program corresponding to the image reconstructing function 83b from the storage circuitry 81, and executing the read program.

Steps S301 and S302 illustrated in FIG. 7 are steps achieved by the processing circuitry 83 by reading the program corresponding to the image reconstructing function 83b from the storage circuitry 81, and executing the read program.

Steps S501 to S505 illustrated in FIG. 14 are steps achieved by the processing circuitry 83 by reading the program corresponding to the image reconstructing function 83b from the storage circuitry 81, and executing the read program.

The term "processor" used in the above explanation means circuitry such as a CPU, a graphic processing unit (GPU), an application specific integrated circuit (ASIC), a programmable logic device (such as a simple programmable logic device: SPLD), a complex programmable logic device (CPLD), and a field programmable gate array (FPGA). The processor achieves the functions thereof by reading and executing the program stored in the storage circuitry. Instead of storing the program in the storage circuitry, the program may be directly incorporated into the circuitry of the processor. In such a case, the processor achieves the functions thereof by reading the program incorporated into the circuitry thereof, and executing the read program.

The modification of the configuration of the X-ray CT apparatus illustrated in FIG. 15 illustrates an example in which a single processor achieves the scan control function 70a, the preprocessing function 70b, the image reconstructing function 70c, and the control function 70d, but the processing circuitry may be configured by combining a plurality of independent processors, to achieve the functions by executing the respective programs by the respective processors. In the same manner, the modification of the configuration of the image processing apparatus illustrated in FIG. 16 illustrates an example in which a single processor achieves the preprocessing function 83a, the image reconstructing function 83b, and the control function 83c, but the processing circuitry may be configured by combining a plurality of independent processors, to achieve the functions by executing the respective programs by the respective processor. The constituent elements in the example of FIG. 15 and the example of FIG. 16 may be integrated into one processor to achieve the functions.

The circuitry illustrated in FIG. 15 and FIG. 16 may be properly divided or integrated. For example, the processing circuitry 70 may be divided into a processing circuitry having the scan control function 70a and the control function 70d, and a processing circuitry having the preprocessing function 70b and the image reconstructing function 70c. The processing circuitry 83 may be divided into a processing circuitry having the control function 83c, and a processing circuitry having the preprocessing function 83a and the image reconstructing function 83b.

The X-ray CT apparatus or the image processing apparatus according to at least one of the embodiments described above enables prompt reconstruction of an enlarged CT image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography (CT) apparatus comprising:
an X-ray detector; and
processing circuitry configured to:
every time any of a plurality of reconstructed CT images which are reconstructed based on X-rays detected by the X-ray detector is designated as a display object image, cause the CT image designated as the display object image to be displayed on a display, and perform preprocessing on raw data corresponding to the CT image designated as the display object image, and
when the processing circuitry receives an enlargement instruction to enlarge the CT image displayed on the display, reconstruct an enlarged CT image using the raw data, which is preprocessed after the CT image is designated as the display object image and before the processing circuitry receives the enlargement instruction, based on the enlargement instruction, and cause the reconstructed enlarged CT image to be displayed on the display, wherein
the processing circuitry causes, until reconstruction of the enlarged CT image is completed, an enlarged image obtained by enlarging the CT image designated as the display object image to be displayed on the display, and causes, after completion of the reconstruction, the enlarged CT image to be displayed on the display.

2. The X-ray CT apparatus according to claim 1, wherein the processing circuitry performs the preprocessing on the raw data corresponding to the plurality of reconstructed CT images including the CT image designated as the display object image, every time any of the CT images is designated as the display object image.

3. The X-ray CT apparatus according to claim 1, wherein the processing circuitry performs at least one of processing to reduce noise and processing to reduce scattered rays on the raw data as the preprocessing.

4. The X-ray CT apparatus according to claim 2, wherein the processing circuitry performs at least one of processing to reduce noise and processing to reduce scattered rays on the raw data as the preprocessing.

5. The X-ray CT apparatus according to claim 1, wherein the processing circuitry also performs convolution to reduce image blurredness on the raw data.

6. The X-ray CT apparatus according to claim 2, wherein the processing circuitry also performs convolution to reduce image blurredness on the raw data.

7. The X-ray CT apparatus according to claim 3, wherein the processing circuitry also performs convolution to reduce image blurredness on the raw data.

8. The X-ray CT apparatus according to claim 4, wherein the processing circuitry also performs convolution to reduce image blurredness on the raw data.

9. The X-ray CT apparatus according to claim 1, wherein the processing circuitry performs initialization every time any of the plurality of reconstructed CT images is designated as the display object image.

10. An image processing apparatus comprising:
processing circuitry configured to:
every time any of a plurality of reconstructed CT images is designated as a display object image, cause the computed tomography (CT) image designated as the display object image to be displayed on a display, and perform preprocessing on raw data corresponding to the CT image designated as the display object image, and
when the processing circuitry receives an enlargement instruction to enlarge the CT image displayed on the display, reconstruct an enlarged CT image using the raw data, which is preprocessed after the CT image is designated as the display object image and before the processing circuitry receives the enlargement instruction, based on the enlargement instruction, and cause the reconstructed enlarged CT image to be displayed on the display, wherein
the processing circuitry causes, until reconstruction of the enlarged CT image is completed, an enlarged image obtained by enlarging the CT image designated as the display object image to be displayed on the display, and causes, after completion of the reconstruction, the enlarged CT image to be displayed on the display.

11. An X-ray computed tomography (CT) apparatus comprising:
processing circuitry configured to:
cause a CT image designated as a display object image to be displayed on a display, every time any of a plurality of reconstructed CT images is designated as the display object image, specify a CT image including an image indicating a certain lesion region among the plurality of reconstructed CT images, and perform preprocessing on raw data corresponding to the specified CT image, and when the processing circuitry receives an enlargement instruction to enlarge the CT image displayed on the display, reconstruct an enlarged CT image using the raw data, which is preprocessed after the CT image including the image indicating the certain lesion region is specified and before the processing circuitry receives the enlargement instruction, and cause the reconstructed enlarged CT image to be displayed on the display, wherein the processing circuitry causes, until reconstruction of the enlarged CT image is completed, an enlarged image obtained by enlarging the CT image designated as the display object image to be displayed on the display, and causes, after completion of the reconstruction, the enlarged CT image to be displayed on the display.

12. The X-ray CT apparatus according to claim 1, wherein the processing circuitry performs the preprocessing on the raw data corresponding to the CT image serving as an object of the enlargement instruction, when the CT image serving as the object of the enlargement instruction is not specified as the CT image including the image indicating the certain lesion region when the processing circuitry receives the enlargement instruction, and reconstructs the enlarged CT image using the raw data, based on the enlargement instruction.

13. The X-ray CT apparatus according to claim 11, wherein the processing circuitry also perform initialization when the processing circuitry specifies the CT image including the image indicating the certain lesion region.

14. The X-ray CT apparatus according to claim 1, further comprising:

a memory configured to store raw data corresponding to the plurality of reconstructed, CT images which are reconstructed based on the X-rays detected by the X-ray detector, wherein the processing circuitry reads the raw data corresponding to the CT image designated as the display object image from the memory, and performs the preprocessing on the read raw data.

* * * * *